United States Patent
Dubief et al.

(10) Patent No.: US 6,375,939 B1
(45) Date of Patent: Apr. 23, 2002

(54) COSMETIC COMPOSITIONS CONTAINING AN AMPHOTERIC POLYMER AND AN ANTIDANDRUFF AGENT, AND USES THEREOF

(75) Inventors: Claude Dubief, Les Chesnay; Serge Restle, Saint-Prix, both of (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 09/602,895

(22) Filed: Jun. 23, 2000

(30) Foreign Application Priority Data

Jun. 25, 1999 (FR) .............................. 99 08173

(51) Int. Cl.⁷ ................................. A61K 7/06
(52) U.S. Cl. .................. 424/70.1; 424/401; 424/70.11; 424/70.16; 514/880; 514/881
(58) Field of Search ................ 424/401, 70.1, 424/70.21, 70.16; 514/880, 881

(56) References Cited

U.S. PATENT DOCUMENTS

| | | | |
|---|---|---|---|
| 2,528,378 A | 10/1950 | Mannheimer | ............ 260/309.6 |
| 2,781,354 A | 2/1957 | Mannheimer | ............ 260/309.6 |
| 4,402,977 A | 9/1983 | Grollier et al. | ................ 424/70 |
| 4,898,725 A * | 2/1990 | Hoeffkes et al. | ............... 424/70 |

FOREIGN PATENT DOCUMENTS

| | | |
|---|---|---|
| DE | 44 04 493 | 1/1995 |
| WO | WO 98/44012 | * 10/1998 |

OTHER PUBLICATIONS

M.R. Porter, "Handbook of Surfactants", Blackie & Son Ltd., Glasgow & London, 1991, pp. 116–178.
English language Derwent Abstract of DE 44 04 493.

* cited by examiner

*Primary Examiner*—Jose' G. Dees
*Assistant Examiner*—Konata M. George
(74) *Attorney, Agent, or Firm*—Finnegan, Henderson, Farabow, Garrett & Dunner, L.L.P.

(57) ABSTRACT

A cosmetic composition containing, in a cosmetically acceptable medium, at least one antidandruff agent and at least one amphoteric polymer containing at least one monomeric unit chosen from (meth)acrylate and (meth)acrylamide types containing at least one fatty chain, the fatty chain containing from 8 to 30 carbon atoms. This combination makes it possible to improve the deposition of the antidandruff agent. These compositions are used for washing and/or conditioning keratin substances such as the hair or the skin.

36 Claims, No Drawings

COSMETIC COMPOSITIONS CONTAINING AN AMPHOTERIC POLYMER AND AN ANTIDANDRUFF AGENT, AND USES THEREOF

The present invention relates to novel cosmetic compositions comprising, in a cosmetically acceptable medium, at least one antidandruff agent and at least one amphoteric polymer comprising at least one monomeric unit chosen from (meth)acrylate and (meth)acrylamide types containing at least one fatty chain, the fatty chain containing from 8 to 30 carbon atoms.

Antidandruff products, which have been proposed in order to combat the formation of dandruff, which is generally accompanied by a microbial and/or fungal proliferation, are either products which inhibit microbial proliferation, or keratolytic products.

However, hair treated with antidandruff agents has a coarse, charged feel. Furthermore, this hair is relatively difficult to disentangle.

In addition, the antifungal activity (in particular with respect to Malassezia Ovalis which is responsible for the formation of dandruff) is still insufficient.

An object of the present invention is thus to propose compositions for effectively combating dandruff while at the same time providing good properties, in particular in terms of softness and disentangling of the hair.

The use of conditioners, in particular cationic or amphoteric polymers or silicones, to make the hair easier to disentangle and to give it softness and suppleness has already been recommended in compositions for washing or caring for keratin substances. However, the cosmetic advantages mentioned above can also unfortunately be accompanied, on dried hair, by certain cosmetic effects that are considered as being undesirable, i.e., an effect of making the hair lank (lack of lightness of the hair) and a lack of smoothness (non-homogeneous hair from the root to the tip).

In addition, the use of cationic polymers for this purpose can present various drawbacks. On account of their high affinity for the hair, some of these polymers can become deposited in large amount during repeated use, and give undesirable effects, such as an unpleasant, charged feel, stiffness of the hair and an inter-fibre adhesion which affects styling. These drawbacks can be accentuated in the case of fine hair, which lacks liveliness and body.

In summary, it is found that the current cosmetic compositions containing antidandruff agents may not entirely be satisfactory.

It has now been discovered that the combination of a specific amphoteric polymer with an antidandruff agent can allow these drawbacks to be overcome or lessened.

Thus, following considerable research conducted in this matter, it has now been found that by introducing a specific amphoteric polymer into the compositions, in particular hair compositions based on antidandruff agents, it is possible to increase the deposition of the antidandruff agent while at the same time improving the cosmetic properties of the compositions based on antidandruff agents.

Without wishing to limit the present invention to any theory, specific interactions and/or affinities would appear to exist between the antidandruff agent, the amphoteric polymers in accordance with the invention and the hair during rinsing. These interactions appear to promote a uniform, sizeable and long-lasting deposition of the antidandruff agents and amphoteric polymers at the surface of the hair. This qualitative and quantitative deposition may be one of the causes of the improvement observed in the final properties, in particular the ease of styling, the hold, the liveliness and the body of the treated hair. All these discoveries form the basis of the present invention.

The compositions in accordance with the invention can give keratin substances, in particular the hair, a noteworthy treating effect which is manifested in particular by one or more of the following properties: ease of disentangling, body, lightness, smoothness, softness, suppleness and hold without any sensation of a charged feel.

Thus, according to the present invention, cosmetic compositions are now proposed comprising, in a cosmetically acceptable medium, at least one antidandruff agent and at least one amphoteric polymer comprising at least one monomeric unit chosen from (meth)acrylate and (meth)acrylamide types containing at least one fatty chain, the fatty chain containing from 8 to 30 carbon atoms.

Another subject of the invention concerns the use of an amphoteric polymer comprising at least one monomeric unit chosen from (meth)acrylate and (meth)acrylamide types containing at least one fatty chain, the fatty chain containing from 8 to 30 carbon atoms, in or for the manufacture of a cosmetic composition comprising an antidandruff agent.

A subject of the invention is also the use of an amphoteric polymer comprising at least one monomeric unit chosen from (meth)acrylate and (meth)acrylamide types containing at least one fatty chain, the fatty chain containing from 8 to 30 carbon atoms, in a composition comprising an antidandruff agent, to increase the efficacy of this antidandruff agent.

The various subjects of the invention will now be detailed. All of the meanings and definitions of the compounds used in the present invention given hereinbelow are valid for all of the subjects of the invention.

The amphoteric polymers according to the invention generally comprise from 1 to 20 mol % of the monomeric units comprising a fatty chain, and preferably from 1.5 to 15 mol % relative to the total number of moles of monomeric units in the polymers, and more particularly from 1.5 to 6 mol %.

The amphoteric polymers according to the invention can result from the copolymerization 1) of at least one monomer chosen from (meth)acrylate and (meth)acrylamide types of formula (Ia) and (Ib):

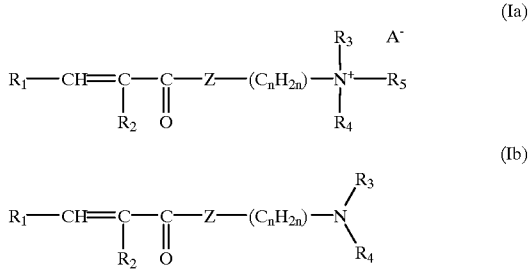

in which:
R$_1$ and R$_2$, which may be identical or different, are a hydrogen atom or a methyl radical; R$_3$, R$_4$ and R$_5$, which may be identical or different, are chosen from linear and branched alkyl radicals containing from 1 to 30 carbon atoms;
Z is an NH group or an oxygen atom;
n is an integer ranging from 2 to 5; and
A$^-$ is an anion derived from an organic or inorganic acid, such as a methyl sulphate anion or a halide such as chloride or bromide, 2) of at least one monomer chosen from (meth)acrylate and (meth)acrylamide types of formula (II)

$$R_6\!-\!CH\!=\!CR_7COOH \qquad (II)$$

in which:
R$_6$ and R$_7$, which may be identical or different, are a hydrogen atom or a methyl radical; and 3) of at least one monomer chosen from (meth)acrylate and (meth)acrylamide types of formula (III):

$$R_6\!-\!CH\!=\!CR_7\!-\!COXR_8 \qquad (III)$$

in which:
R$_6$ and R$_7$, which may be identical or different, are a hydrogen atom or a methyl radical; X is an oxygen or nitrogen atom; and R$_8$ is chosen from linear and branched alkyl radicals containing from 1 to 30 carbon atoms;
at least one of the (meth)acrylate and (meth)acrylamide type monomers of formula (Ia), (Ib) or (III) comprises at least one fatty chain containing from 8 to 30 carbon atoms.

The monomers of formulae (Ia) and (Ib) of the present invention are preferably chosen from:
dimethylaminoethyl methacrylate, dimethylaminoethyl acrylate,
diethylaminoethyl methacrylate, diethylaminoethyl acrylate,
dimethylaminopropyl methacrylate, dimethylaminopropyl acrylate, and
dimethylaminopropylmethacrylamide, dimethylaminopropylacrylamide,
these monomers optionally being quaternized, for example with a (C$_1$–C$_4$) alkyl halide or a (C$_1$–C$_4$) dialkyl sulphate.

More particularly, the monomer of formula (Ia) is chosen from
acrylamidopropyltrimethylammonium chloride and methacrylamidopropyltrimethylammonium chloride.

The monomers of formula (II) of the present invention are preferably chosen from acrylic acid, methacrylic acid, crotonic acid and 2-methylcrotonic acid.

The monomer of formula (II) is more particularly acrylic acid.

The monomers of formula (III) of the present invention are preferably chosen from (C$_{12}$–C$_{22}$) and more particularly (C$_{16}$–C$_{18}$) alkyl acrylates or methacrylates.

The monomers constituting the amphoteric polymers of the invention are preferably already neutralized and/or quaternized.

The ratio of the number of cationic charges/anionic charges is preferably equal to about 1.

The amphoteric polymers according to the invention preferably comprise from 1 to 10 mol % of monomeric units comprising a fatty chain (monomer of formula (Ia), (Ib) or (III), and preferably from 1.5 to 6 mol %.

The weight-average molecular weights of the amphoteric polymers according to the invention can range from 500 to 50,000,000 and preferably range from 10,000 and 5,000,000.

The polymers according to the invention can also contain other monomers such as nonionic monomers and in particular such as (C$_1$–C$_4$) alkyl acrylates or methacrylates.

The amphoteric polymers according to the invention are described, for example, in patent application WO 98/44012, the disclosure of which is hereby incorporated by reference.

The amphoteric polymers that are particularly preferred according to the invention are chosen from acrylic acid/ acrylamidopropyltrimethylammonium chloride/stearyl methacrylate copolymers.

The amphoteric polymer is preferably used in the composition in an amount ranging from 0.05 to 10% by weight relative to the total weight of the composition. This amount is more preferably from 0.1 to 5% by weight relative to the total weight of the composition.

The antidandruff agents can be any active agent which is useful for preventing the appearance of dandruff, for reducing its amount and/or for making it disappear altogether. Thus, the antidandruff agent can be chosen from antifungal agents and/or antibacterial agents.

The antidandruff agents which can be used according to the invention are chosen in particular from:

1) Pyridinethione salts, in particular the calcium, magnesium, barium, strontium, zinc, cadmium, tin and zirconium salts. The zinc salt of pyridinethione is particularly preferred.

The zinc salt of pyridinethione is sold in particular under the name ZINC OMADINE by the company OLIN.

2) 1-Hydroxy-2-pyrrolidone derivatives represented by formula (IV):

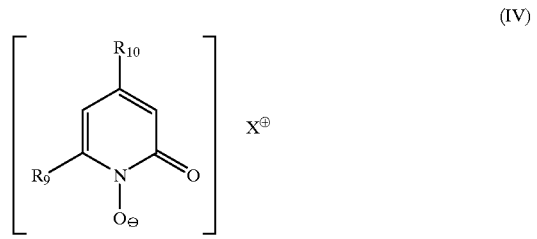

(IV)

in which:
R$_9$ is chosen from an alkyl group containing from 1 to 17 carbon atoms, an alkenyl group containing from 2 to 17 carbon atoms, a cycloalkyl group containing from 5 to 8 carbon atoms, a bicycloalkyl group containing from 7 to 9 carbon atoms, a cycloalkyl (alkyl) group, an aryl group wherein the aryl may have as possible substituents a halogen group, a nitro group, and a cyano group, an aralkyl group wherein the alkyl contains from 1 to 4 carbon atoms, an arylalkenyl group wherein the alkenyl contains from 2 to 4 carbon atoms, an aryloxyalkyl wherein the alkyl contains from 1 to 4 carbon atoms, arylmercaptoalkyl group wherein the alkyl contains from 1 to 4 carbon atoms, a furylalkenyl group wherein the alkenyl contains from 2 to 4 carbon atoms or wherein the furyl contains from 2 to 4 carbon atoms, an alkoxy group containing from 1 to 4 carbon atoms, a nitro group, a cyano group and a halogen atom;
R$_{10}$ is chosen from a hydrogen atom, a (C$_1$–C$_4$) alkyl group, a (C$_2$–C$_4$) alkenyl group, a halogen atom, a phenyl group, and a benzyl group; and
X$^+$ is chosen from a quaternized organic base, an alkali metal ion, alkaline-earth metal ion, and an ammonium ion.

Compounds of formula (IV) are, for example, 1-hydroxy-4-methyl-2-pyridone, 1-hydroxy-6-methyl-2-pyridone, 1-hydroxy-4,6-dimethyl-2-pyridone, 1-hydroxy-4-methyl-6-(2,4,4-trimethylpentyl)-2-pyridone, 1-hydroxy-4-methyl-6-cyclohexyl-2-pyridone, 1-hydroxy-4-methyl-6-(methylcyclohexyl)-2-pyridone, 1-hydroxy-4-methyl-6-(2- bicyclo (2,2,1) heptyl)-2-pyridone, 1-hydroxy-4-methyl-6-(4-methylphenyl)-2-pyridone, 1-hydroxy-4-methyl-6-(1-(4-nitrophenoxy)butyl)-2-pyridone, 1-hydroxy-4-methyl-6-(4-cyanophenoxymethyl)-2-pyridone, 1-hydroxy-4-methyl-6-(phenylsulphonylmethyl)-2-pyridone or 1-hydroxy-4-methyl-6-(4-bromobenzyl)-2-pyridone.

The compounds of formula (IV) can be used in the form of salts with organic or inorganic bases.

Examples of organic bases are, in particular, alkanolamines of low molecular weight, such as ethanolamine, diethanolamine, N-ethylethanolamine, triethanolamine, diethylaminoethanol and 2-amino-2-methylpropanediol; non-volatile bases, such as ethylenediamine, hexamethylenediamine, cyclohexylamine, benzylamine and N-methylpiperazine; quaternary ammonium hydroxides, such as trimethylbenzyl hydroxide; guanidine and its derivatives, and in particular its alkyl derivatives. Examples of inorganic bases are, in particular, alkali metal salts, such as sodium and potassium salts; ammonium salts, alkaline-earth metal, salts such as magnesium and calcium salts; salts of divalent, trivalent or tetravalent cationic metals, such as zinc, aluminium or zirconium. The alkanolamines, ethylene-diamine and inorganic bases, such as the alkali metal salts are preferred.

One compound of formula (IV) that is particularly preferred is the one for which $R_9$ is a radical

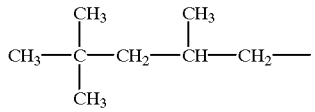

$R_{10}$ is a methyl group
and $X^+$ a $N^+H_3CH_2CH_2OH$.

This compound is sold, for example, under the name OCTOPIROX (1-hydroxy4-methyl-6-(2,4,4-trimethylpentyl)-2-pyridone, monoethanolamine salt) by the company Hoechst.

3) 2,2'-Dithiobis(pyridine N-oxide) of formula (V):

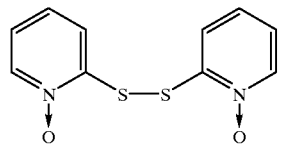

(V)

The compounds of formula (V) can be introduced into the composition in the form of inorganic salts. An example of an inorganic salt is magnesium sulphate.

4) Trihalocarbamides of formula (VI) below:

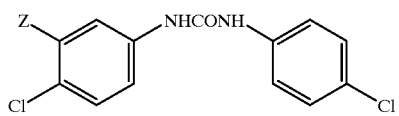

(VI)

in which:
  Z is a halogen atom, such as chlorine or a ($C_1$–$C_4$) trihaloalkyl group such as $CF_3$.

5) Triclosan, represented by formula (VII):

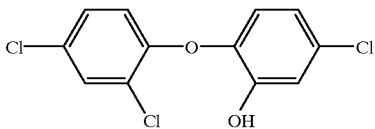

(VII)

6) Azo compounds, such as climbazole, ketoconazole, clotrinazole, econazole, isoconazole and miconazole.
7) Antifungal polymers, such as amphotericin B or nystatin.
8) Selenium sulphide.
9) Other antidandruff agents are sulphur in its various forms, cadmium sulphide, allantoin, coal tars or wood tars and derivatives thereof, in particular cade oil, salicylic acid, undecylenic acid, fumaric acid and allylamines, such as terbinafine.

ZINC OMADOINE, OCTOPIROX and selenium sulphide are particularly preferred.

According to the invention, the antidandruff agent(s) can represent from 0.001% to 20% by weight, preferably from 0.01% to 10% by weight and more particularly from 0.1 to 5% by weight, relative to the total weight of the final composition.

The composition of the invention also advantageously contains at least one surfactant which is generally present in the composition in an amount ranging from 0.1% to 60% by weight approximately, preferably from 3% to 40% and even more preferably from 5% to 30%, relative to the total weight of the composition.

This surfactant can be chosen from anionic, amphoteric and nonionic surfactants, or mixtures thereof.

The surfactants which are suitable for carrying out the present invention are, in particular, the following:
  (i) Anionic surfactant(s):

In the context of the present invention, their nature is not of truly critical importance.

Thus, as examples of anionic surfactants which can be used, alone or mixed, in the context of the present invention, mention may be made in particular (non-limiting list) of salts (in particular alkaline salts, especially sodium salts, ammonium salts, amine salts, amino alcohol salts or magnesium salts) of the following compounds: alkyl sulphates, alkyl ether sulphates, alkylamidoether sulphates, alkylarylpolyether sulphates, monoglyceride sulphates; alkylsulphonates, alkyl phosphates, alkylamide sulphonates, alkylaryl sulphonates, α-olefin sulphonates, paraffin sulphonates; alkyl sulphosuccinates; alkyl ether sulphosuccinates; alkylamide sulphosuccinates; alkyl sulphosuccinamates; alkyl sulphoacetates; alkyl ether phosphates; acylsarcosinates; acylisethionates and N-acyltaurates, the alkyl or acyl radical of all these various compounds preferably containing from 8 to 24 carbon atoms, and the aryl radical preferably denoting a phenyl or benzyl group. Among the anionic surfactants which can also be used, mention may also be made of fatty acid salts such as the salts of oleic, ricinoleic, palmitic or stearic acid, coconut oil acid or hydrogenated coconut oil acid; acyl lactylates in which the acyl radical contains 8 to 20 carbon atoms. Weakly anionic surfactants can also be used, such as alkyl D-galactosiduronic acids and their salts, as well as polyoxyalkylenated ($C_6$–$C_{24}$) alkyl ether carboxylic acids, polyoxyalkylenated ($C_6$–$C_{24}$) alkylaryl ether carboxylic acids, polyoxyalkylenated ($C_6$–$C_{24}$) alkylamido ether carboxylic acids and their salts, in particular those comprising from 2 to 50 ethylene oxide groups, and mixtures thereof.

Among the anionic surfactants which are preferably used according to the invention are the salts of alkyl sulphates and of alkyl ether sulphates and mixtures thereof.

(ii) Nonionic surfactant(s):

Nonionic surfactants are, themselves also, compounds that are well known per se (see in particular in this respect "Handbook of Surfactants" by M. R. Porter, published by Blackie & Son (Glasgow and London), 1991, pp. 116–178, the disclosure of which is incorporated by reference), and in the context of the present invention, their nature is not of critical importance. Thus, they can be chosen in particular from (non-limiting list) polyethoxylated, polypropoxylated or polyglycerolated alcohols, alpha-diols, alkylphenols or fatty acids containing a fatty chain containing, for example, 8 to 18 carbon atoms, the number of ethylene oxide or propylene oxide groups possibly ranging in particular from 2 to 50 and the number of glycerol groups possibly ranging in particular from 2 to 30. Mention may also be made of copolymers of ethylene oxide and of propylene oxide, condensates of ethylene oxide and of propylene oxide with fatty alcohols; polyethoxylated fatty amides preferably containing from 2 to 30 mol of ethylene oxide, polyglycerolated fatty amides comprising on average 1 to 5 and in particular 1.5 to 4 glycerol groups; polyethoxylated fatty amines preferably containing 2 to 30 mol of ethylene oxide; oxyethylenated fatty acid esters of sorbitan containing from 2 to 30 mol of ethylene oxide; fatty acid esters of sucrose, fatty acid esters of polyethylene glycol, alkylpolyglycosides, N-alkylglucamine derivatives, amine oxides such as $(C_{10}-C_{14})$alkylamine oxides or N-acylaminopropylmorpholine oxides. It will be noted that the alkylpolyglycosides constitute nonionic surfactants that are particularly suitable in the context of the present invention.

(iii) Amphoteric surfactant(s):

The amphoteric surfactants, whose nature, in the context of the present invention, is not of critical importance, can be, in particular (non-limiting list), aliphatic secondary or tertiary amine derivatives, in which the aliphatic radical is a linear or branched chain containing 8 to 22 carbon atoms and containing at least one water-solubilizing anionic group (for example carboxylate, sulphonate, sulphate, phosphate or phosphonate); mention may also be made of $(C_8-C_{20})$alkyl betaines, sulphobetaines, $(C_8-C_{20})$alkylamido$(C_1-C_6)$alkylbetaines or $(C_8-C_{20})$alkylamido$(C_1-C_6)$alkylsulphobetaines.

Among the amine derivatives which may be mentioned are the products sold under the name MIRANOL, as described in U.S. Pat. Nos. 2,528,378 and 2,781,354, the disclosures of both of which are hereby incorporated by reference, and of structures:

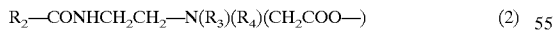

$$R_2\text{—CONHCH}_2\text{CH}_2\text{—N}(R_3)(R_4)(CH_2COO\text{—}) \quad (2)$$

in which:

R$_2$ is an alkyl, preferably an alkyl radical of an acid R$_2$—COOH present in hydrolysed coconut oil, or a heptyl, nonyl or undecyl radical; R$_3$ is a beta-hydroxyethyl group; and R$_4$ is a carboxymethyl group; and

$$R_5\text{—CONHCH}_2\text{CH}_2\text{—N(B)(C)} \quad (3)$$

in which:

B is —CH$_2$CH$_2$OX', C is —(CH$_2$)$_z$—Y', with z being equal to 1 or 2,

X' is a —CH$_2$CH$_2$—COOH group or a hydrogen atom,

Y' is —COOH or a —CH$_2$—CHOH—SO$_3$H radical,

R$_5$ is an alkyl, preferably, an alkyl radical of an acid R$_5$—COOH present in coconut oil or in hydrolysed linseed oil, or a C$_7$, C$_9$, C$_{11}$ or C$_{13}$ alkyl radical, or a C$_{17}$ alkyl radical and its iso form, or an unsaturated C$_{17}$ radical.

The compounds are classified in the CTFA dictionary, 5th edition, 1993, the disclosure of which is hereby incorporated by reference, under the names Disodium Cocoamphodiacetate, Disodium Lauroamphodiacetate, Disodium Caprylamphodiacetate, Disodium Caprylamphodiacetate, Disodium Cocoamphodipropionate, Disodium Lauroamphodipropionate, Disodium Caprylamphodipropionate, Disodium Caprylloamphodipropionate, Lauroamphodipropionic acid and Cocoamphodipropionic acid.

By way of example, mention may be made of cocoamphodiacetate sold under the trade name MIRANOL C2M concentrate by the company Rhône Poulenc.

Mixtures of surfactants and in particular mixtures of anionic surfactants and mixtures of anionic surfactants and amphoteric or nonionic surfactants are preferably used in the compositions in accordance with the invention. One mixture which is particularly preferred is a mixture comprising at least one anionic surfactant and at least one amphoteric surfactant.

The anionic surfactant preferably used is chosen from sodium, triethanolamine or ammonium $(C_{12}-C_{14})$alkyl sulphate, sodium, triethanolamine or ammonium $(C_{12}-C_{14})$ alkyl ether sulphate oxyethylenated with 2.2 mol of ethylene oxide, sodium cocoylisethionate and sodium alpha-$(C_{14}-C_{16})$olefin sulphonate and mixtures thereof with:

either an amphoteric surfactant such as the amine derivatives known as disodium cocoamphodipropionate or sodium cocoamphopropionate sold in particular by the company Rhône Poulenc under the trade name MIRANOL C2M CONC. as an aqueous solution containing 38% active material, or under the name MIRANOL C32;

or an amphoteric surfactant of zwitterionic type such as alkylbetaines, in particular the cocobetaine sold under the name DEHYTON AB 30 as an aqueous solution containing 32% AM, by the company Henkel.

The composition of the invention can also contain at least one additive chosen from thickeners, fragrances, nacreous agents, preserving agents, silicone sunscreens, non-silicone sunscreens, vitamins, mineral waxes, cationic, anionic polymers, nonionic polymers, proteins, protein hydrolysates, fatty acids containing a linear $(C_{16}-C_{40})$ chain and fatty acids containing a branched $(C_{16}-C_{40})$ chain, such as 18-methyleicosanoic acid, fatty acid esters, cationic surfactants; fatty alcohols, hydroxy acids, panthenol, animal oils, mineral oils, synthetic oils, plant oils, compounds of ceramide type and any other additive conventionally used in cosmetics which does not affect substantially adversely the properties of the compositions according to the invention.

These additives are present in the composition according to the invention in proportions which can range from 0 to 20% by weight relative to the total weight of the composition. The precise amount of each additive is readily determined by a person skilled in the art depending on its nature and its function.

The compositions in accordance with the invention can be used more particularly for washing or treating keratin substances, such as the hair. They can be used on the scalp, the skin, the eyelashes, the eyebrows, the nails and the lips.

In particular, the compositions according to the invention are detergent compositions such as shampoos, shower gels and bubble baths. In this embodiment of the invention, the compositions comprise a washing base, which is generally aqueous.

The surfactant(s) forming the washing base can be chosen, without preference, alone or as mixtures, from the anionic, amphoteric, nonionic and cationic surfactants as defined above.

The quantity and quality of the washing base are those which are sufficient to give the final composition satisfactory foaming power and/or detergent power.

Thus, according to the invention, the washing base can represent from 4% to 50% by weight, preferably from 6% to 35% by weight and even more preferably from 8% to 25% by weight, relative to the total weight of the final composition.

A subject of the invention is also a process for treating keratin substances, such as the skin or the hair, comprising applying to the keratin substances a cosmetic composition as defined above, and then in optionally rinsing with water.

Thus, this process according to the invention allows holding of the hairstyle, the treatment, care, washing or removal of make-up from the skin or the hair or from any other keratin substance.

The compositions of the invention can also be in the form of a rinse-out or leave-in conditioner, permanent-waving, straightening, dyeing or bleaching compositions for the hair, or alternatively in the form of rinse-out compositions to be applied before or after dyeing, bleaching, permanent-waving or straightening the hair or else between two steps of a permanent-waving or hair-straightening operation.

The compositions of the invention can also be in the form of washing compositions for the skin, and in particular in the form of bath or shower solutions or gels or make-up-removing products.

The compositions according to the invention can also be in the form of aqueous or aqueous-alcoholic lotions for skincare and/or haircare.

The cosmetic compositions according to the invention can be in the form of a gel, a milk, a cream, an emulsion, a thickened lotion or a mousse.

The compositions can be packaged in various forms, in particular in vaporizers, pump-dispenser bottles or in aerosol cans in order to apply the composition in vaporized form or in the form of a mousse. Such packaging forms are indicated, for example, when it is desired to obtain a spray, a lacquer or a mousse for treating the hair.

Throughout the text hereinabove and hereinbelow, the percentages are expressed on a weight basis.

The invention will now be illustrated more fully with the aid of the example which follows, which should not be considered as limiting it to the embodiments described. In the example, AM means active material.

EXAMPLE

A shampoo of the composition below was prepared:

| | |
|---|---|
| Sodium lauryl ether sulphate (2.2 EO) | 17 g AM |
| Cocoylbetaine as an aqueous 30% solution (DEHYTON AB 30 from Henkel) | 2.5 g AM |
| Terpolymer of methacrylamidopropyl-trimethylammonium chloride, acrylic acid and stearyl methacrylate (49 mol %/49 mol %/2 mol %) | 1 g AM |

-continued

| | |
|---|---|
| Sodium cetostearyl sulphate | 0.75 g |
| Coconut acid monoisopropanolamide | 0.6 g |
| 1-Hydroxy-4-methyl-6-trimethylpentyl-2-pyridone (OCTOPIROX from Clariant) | 0.5 g AM |
| Preserving agents, fragrance | qs |
| Water qs | 100 g |

What is claimed is:

1. A cosmetic composition comprising at least one antidandruff agent and at least one amphoteric polymer comprising at least one monomeric unit chosen from (meth)acrylate and (meth)acrylamide types containing at least one fatty chain, the fatty chain containing from 8 to 30 carbon atoms.

2. The composition according to claim 1, further comprising a cosmetically acceptable medium.

3. The composition according to claim 1, wherein the at least one amphoteric polymer comprises from 1 to 20 mol % of monomeric units comprising a fatty chain relative to the total number of moles of monomeric units in said at least one polymer.

4. The composition according to claim 3, wherein the at least one amphoteric polymer comprises from 1.5 to 15 mol % of monomeric units comprising a fatty chain relative to the total number of moles of monomeric units in said at least one polymer.

5. The composition according to claim 1, wherein the at least one amphoteric polymer results from copolymerization:

1) of at least one monomer chosen from (meth)acryate and (meth)acrylamide types of formula (Ia) and (Ib):

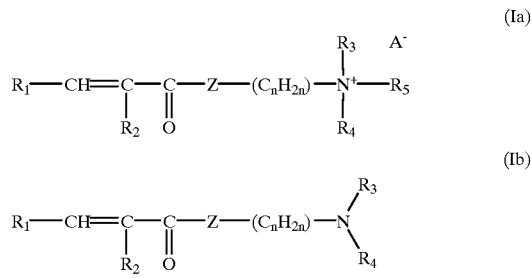

in which;

$R_1$ and $R_2$, which may be identical or different, are a hydrogen atom or a methyl radical; $R_3$, $R_4$ and $R_5$, which may be identical or different, are chosen from linear and branched alkyl radicals containing from 1 to 30 carbon atoms;

Z is an NH group or an oxygen atom;

n is an integer ranging from 2 to 5; and $A^-$ is an anion derived from an organic or inorganic acid, 2) of at least one monomer chosen from (meth)acylate and (meth)acrylamide types of formula (II)

$$R_6\text{—CH}=\text{CR}_7\text{—COOH} \qquad (II)$$

in which;

$R_6$ and $R_7$, which may be identical or different, are a hydrogen atom or a methyl radical; and 3) of at least one monomer chosen from (meth)acylate and (meth)acrylamide types of formula (III):

$$R_6—CH=CR_7—COXR_8 \quad (III)$$

in which;
R$_6$ and R$_7$, which may be identical or different, are a hydrogen atom or a methyl radical; X is an oxygen or nitrogen atom; and R$_8$ is chosen from linear and branched alkyl radicals containing from 1 to 30 carbon atoms;
wherein at least one of the (meth)acrylate and (meth)acylamide type monomers of formula (Ia), (Ib) or (III) comprise at least one fatty chain containing from 8 to 30 carbon atoms.

6. The composition according to claim 5, wherein the at least one monomer of formula (Ia) and (Ib) is chosen from:
dimethylaminoethyl methacrylate, dimethylaminoethyl acrylate,
diethylaminoethyl methacrylate, diethylaminoethyl acrylate,
dimethylaminopropyl methacrylate, dimethylaminopropyl acrylate, and
dimethylaminopropylmethacrylamide, dimethylaminopropylacrylamide,
these monomers optionally being quaternized.

7. The composition according to of claim 5, wherein the at least one monomer of formula (Ia) is chosen from acrylamidopropyltrimethylammonium chloride and methacrylamidopropyltrimethylammonium chloride.

8. The composition according to claim 5, wherein the at least one monomer of formula (II) is chosen from acrylic acid, methacrylic acid, crotonic acid and 2-methylcrotonic acid.

9. The composition according to claim 5, wherein the at least one monomer of formula (III) is chosen from (C$_{12}$–C$_{22}$) alkyl acrylates and methacrylates.

10. The composition according to claim 9, wherein the at least one monomer of formula (III) is chosen from (C$_{16}$–C$_{18}$) alkyl acrylates and methacrylates.

11. The composition according to claim 1, wherein the at least one amphoteric polymer is chosen from acrylic acid/acrylamidopropyltrimethylammonium chloride/stearyl methacrylate copolymers.

12. The composition according to claim 1, wherein the at least one amphoteric polymer is present in the composition in an amount ranging from 0.05 to 10% by weight relative to the total weight of the composition.

13. The composition according to claim 1, wherein the at least one antidandruff agent is chosen from antifungal agents and antibacterial agents.

14. The composition according to claim 1, wherein the at least one antidandruff agent is chosen from:
1) pyridinethione salts,
2) 1-hydroxy-2-pyrrolidone derivatives represented by formula (IV):

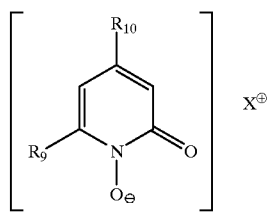

(IV)

in which:
R$_9$ is chosen from an alkyl group containing from 1 to 17 carbon atoms, an alkenyl group containing from 2 to 17 carbon atoms, a cycloalkyl group containing from 5 to 8 carbon atoms, a bicycloalkyl group containing from 7 to 9 carbon atoms, a cycloalkyl (alkyl) group, an aryl group wherein the aryl may have as possible substituents a halogen group, a nitro group, and a cyano group, an aralkyl group wherein the alkyl contains from 1 to 4 carbon atoms, an arylalkenyl group wherein the alkenyl contains from 2 to 4 carbon atoms, an aryloxyalkyl wherein the alkyl contains from 1 to 4 carbon atoms, arylmercaptoalkyl group wherein the alkyl contains from 1 to 4 carbon atoms, a furylalkenyl group wherein the alkenyl contains from 2 to 4 carbon atoms and wherein the furyl contains from 2 to 4 carbon atoms, an alkoxy group containing from 1 to 4 carbon atoms, a nitro group, a cyano group and a halogen atom;
R$_{10}$ chosen from a hydrogen atom, a (C$_1$–C$_4$) alkyl group, a (C$_2$–C$_4$) alkenyl group, a halogen atom, a phenyl group, a benzyl group; X$^+$ is chosen from a quaternized organic base, an alkali metal ion, alkaline-earth metal ion, and an ammonium ion, 3) 2,2'-dithiobis(pyridine N-oxide) of formula (V):

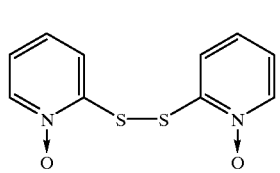

(V)

4) trihalocarbamides of formula (VI):

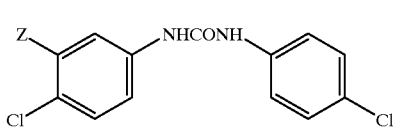

(VI)

in which Z is a halogen atom,
5) triclosan, represented by formula (VII):

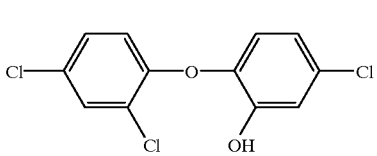

(VII)

6) azo compounds,
7) antifungal polymers,
8) selenium sulphide, and
9) other antidandruff agents chosen from sulphur in its various forms, cadmium sulphide, allantoin, coal tar, wood tar and derivatives thereof.

15. The composition according to claim 14, wherein the pyridinethione salts are chosen from calcium, magnesium, barium, strontium, zinc, cadmium, tin, and zirconium salts.

16. The composition according to claim 14, wherein Z in formula (VI) is a chlorine group or a (C$_1$–C$_4$) trihaloalkyl group.

17. The composition according to claim 16, wherein the ($C_1$–$C_4$) trihaloalkyl group is $CF_3$.

18. The composition according to claim 14, wherein the azo compounds are chosen from climbazole, ketoconazole, clotrinazole, econazole, isoconazole, and miconazole.

19. The composition according to claim 14, wherein the antifungal polymers are chosen from amphotericin B and mystatin.

20. The composition according to claim 14, wherein the other antidandruff agents are chosen from cade oil, salicyclic acid, undecylenic acid, fumaric acid, and allylamines.

21. The composition according to claim 20, wherein the allylamines are chosen from terbinafines.

22. The composition according to claim 14, wherein the at least one antidandruff agent is chosen from:

a zinc salt of pyridinethione 1-hydroxy-4-methyl-6-(2,4,4-trimethylpentyl)-2-pyridone, and selenium sulphide.

23. The composition according to claim 1, wherein the at least one antidandruff agent is present in the composition in a concentration ranging from 0.001% to 20% by weight relative to the total weight of the composition.

24. The composition according to claim 23, wherein the at least one antidandruff agent is present in the composition in a concentration ranging from 0.01% to 10% by weight relative to the total weight of the composition.

25. The composition according to claim 1, wherein the composition also comprises at least one surfactant.

26. The composition according to claim 25, wherein the at least one surfactant is present in the composition in a concentration ranging from 0.1% to 60% by weight relative to the total weight of the composition.

27. The composition according to claim 26, wherein the at least one surfactant is present in the composition in a concentration ranging from 3% to 40% by weight relative to the total weight of the composition.

28. The composition according to claim 1, wherein the composition also comprises at least one additive chosen from thickeners, fragrances, nacreous agents, preserving agents, silicone sunscreens, non-silicone sunscreens, vitamins, mineral waxes, cationic, anionic polymers, non-ionic polymers, proteins, protein hydrolysates, fatty acids containing a linear ($C_{16}$–$C_{40}$) chain, fatty acids containing a branched ($C_{16}$–$C_{40}$) chain, fatty acid esters, fatty alcohols, hydroxy acids, panthenol, cationic surfactants, animal oils, mineral oils, synthetic oils, plant oils, compounds of ceramide type, and any other additive conventionally used in cosmetics.

29. The composition according to claim 28, wherein the at least one additive is 18-methyleicosanoic acid.

30. A shampoo, a conditioner, a composition for permanent-waving hair, a composition for straightening hair, a composition for dyeing hair, a composition for bleaching hair, a rinse-out composition to be applied between two steps of a permanent-waving operation or hair-straightening operation, or a composition for the skin comprising:

at least one antidandruff agent and at least one amphoteric polymer comprising at least one monomeric unit chosen from (meth)acrylate and (meth)acrylamide types containing at least one fatty chain, the fatty chain containing from 8 to 30 carbon atoms.

31. A method for washing or caring for a keratin substance comprising applying to the keratin substance a composition comprising at least one antidandruff agent, and at least one amphoteric polymer comprising at least one monomeric unit chosen from (meth)acrylate and (meth)acrylamide types containing at least one fatty chain, the fatty chain containing from 8 to 30 carbon atoms.

32. A treatment process for a keratin substance comprising applying to the substance a composition comprising at least one antidandruff agent, and at least one amphoteric polymer comprising at least one monomeric unit chosen from (meth)acrylate or (meth)acrylamide types containing at least one fatty chain, the fatty chain containing from 8 to 30 carbon atoms, and then optionally rinsing with water.

33. The treatment process according to claim 32, wherein the keratin substance is hair.

34. A method of increasing the efficacy of an antidandruff agent comprising including in a composition comprising at least one antidandruff agent at least one amphoteric polymer comprising one monomeric unit chosen from (meth)acrylate and (meth)acrylamide types containing at least one fatty chain, the fatty chain containing from 8 to 30 carbon atoms.

35. A method of making a cosmetic composition comprising an antidandruff agent comprising combining at least one amphoteric polymer comprising at least at one monomeric unit chosen from (meth)acrylate and (meth)acrylamide types containing at least one fatty chain, the fatty chain containing from 8 to 30 carbon atoms to a composition with at least one antidandruff agent.

36. The cosmetic composition according to claim 1, wherein the combination of the at least one antidandruff agent and the at least one amphoteric polymer increases the efficacy of the antidandruff agent.

* * * * *

UNITED STATES PATENT AND TRADEMARK OFFICE
CERTIFICATE OF CORRECTION

PATENT NO. : 6,375,939 B1
DATED : April 23, 2002
INVENTOR(S) : Claude Dubief et al.

It is certified that error appears in the above-identified patent and that said Letters Patent is hereby corrected as shown below:

Column 10,
Line 34, "(meth)acryate" should read -- (meth)acrylate --.
Line 59, "(meth)acylate" should read -- (meth)acrylate --.

Column 11,
Line 1, "(meth)acylate" should read -- (meth)acrylate --.
Lines 11 and 12, "(meth)acylamide" should read -- (meth)acrylamide --.
Line 26, "to of claim" should read -- to claim --.

Column 14,
Line 36, before "one monomeric" insert -- at least --.
Line 43, before "one monomeric" delete "at".

Signed and Sealed this

Thirteenth Day of August, 2002

*Attest:*

JAMES E. ROGAN
*Attesting Officer*     *Director of the United States Patent and Trademark Office*